United States Patent
Canestrini

(10) Patent No.: US 9,943,153 B2
(45) Date of Patent: Apr. 17, 2018

(54) APPLICATOR AND A DYE KIT COMPRISING SAID APPLICATOR

(71) Applicant: CLOZ MANAGEMENT AB, Karlstad (SE)

(72) Inventor: Cristina Canestrini, Hammaro (SE)

(73) Assignee: CLOZ Management AB (SE)

( * ) Notice: Subject to any disclaimer, the term of this patent is extended or adjusted under 35 U.S.C. 154(b) by 0 days.

(21) Appl. No.: 15/110,393

(22) PCT Filed: Feb. 6, 2015

(86) PCT No.: PCT/SE2015/050135
§ 371 (c)(1),
(2) Date: Jul. 7, 2016

(87) PCT Pub. No.: WO2015/119565
PCT Pub. Date: Aug. 13, 2015

(65) Prior Publication Data
US 2016/0331100 A1 Nov. 17, 2016

(30) Foreign Application Priority Data
Feb. 7, 2014 (SE) ...................... 1450128

(51) Int. Cl.
*B05C 11/00* (2006.01)
*A45D 19/02* (2006.01)
(Continued)

(52) U.S. Cl.
CPC ............. *A45D 19/02* (2013.01); *A45D 19/00* (2013.01); *A45D 40/28* (2013.01);
(Continued)

(58) Field of Classification Search
CPC ...... A45D 19/02; A45D 40/28; A61M 35/003
(Continued)

(56) References Cited

U.S. PATENT DOCUMENTS 2,008,636 A * 7/1935 Brynan ................. B65D 35/36
401/262
4,495,958 A 1/1985 Roeder
(Continued)

FOREIGN PATENT DOCUMENTS

FR      1185116 A      7/1959
JP      08107808 A * 4/1996
(Continued)

OTHER PUBLICATIONS

International Search Report issued in International Application No. PCT/SE2015/050135 dated Jun. 9, 2015.
(Continued)

*Primary Examiner* — Jennifer C Chiang
(74) *Attorney, Agent, or Firm* — Eric L. Sophir; Dentons US LLP

(57) ABSTRACT

An applicator for applying a product to head hair comprises a neck portion and a flexible/elastic spatula. The neck portion comprises inner threads and an upper end and the spatula comprises a free end at a distal end from said neck portion. The free end comprises an edge extending in a substantially orthogonal direction to the extension of the spatula, said edge having a dispensing opening. The spatula forms a flat shaped body portion between said neck portion and said flat shaped body portion. The applicator comprises a bridging portion, comprising a bottom extending in a substantially transversal direction to the neck portion. The substantially flat shaped body portion extends in a substantially orthogonal direction from said bottom, defining an internal channel extending from the dispensing opening to an inlet opening. The inlet opening is arranged at the lower side of the bottom in the interior of the neck portion.

11 Claims, 3 Drawing Sheets

(51) Int. Cl.
*A45D 19/00* (2006.01)
*A61M 35/00* (2006.01)
*A45D 40/28* (2006.01)

(52) U.S. Cl.
CPC ... *A61M 35/003* (2013.01); *A45D 2019/0066* (2013.01); *A45D 2019/0083* (2013.01); *A45D 2200/25* (2013.01)

(58) Field of Classification Search
USPC .................................................. 401/265, 266
See application file for complete search history.

(56) References Cited

U.S. PATENT DOCUMENTS

| 6,526,987 B1 | 3/2003 | Gioia |
| 2001/0042553 A1 | 11/2001 | Duqueroie |
| 2004/0016440 A1 | 1/2004 | De Laforcade et al. |
| 2004/0221864 A1 | 11/2004 | Capristo |

FOREIGN PATENT DOCUMENTS

| WO | 01/35789 A1 | 5/2001 |
| WO | 2010/046921 A2 | 4/2010 |
| WO | 2011/085061 A1 | 7/2011 |

OTHER PUBLICATIONS

Written Opinion of the International Searching Authority issued in International Application No. PCT/SE2015/050135 dated Jun. 9, 2015.
Supplementary European Search Report dated Aug. 18, 2017 in corresponding European Application No. EP 15 74 6726, 7 pages.

\* cited by examiner

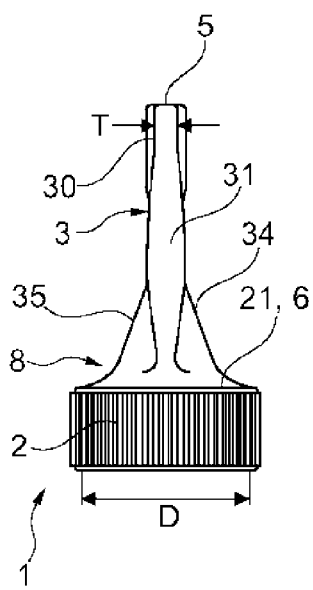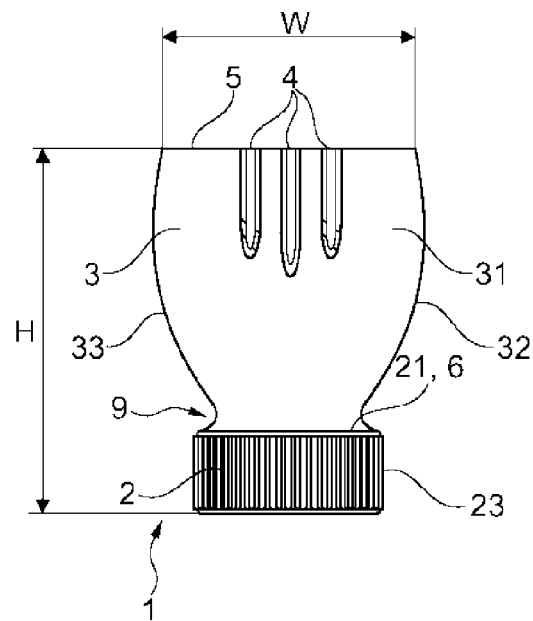
Fig. 1        Fig. 2
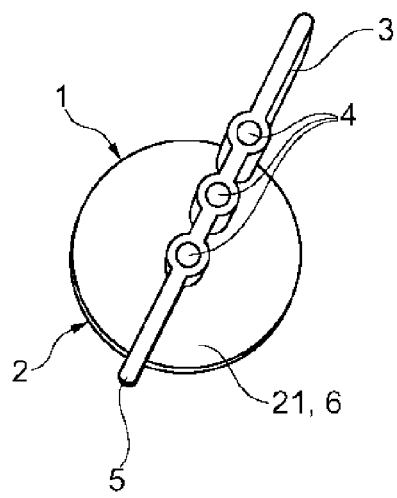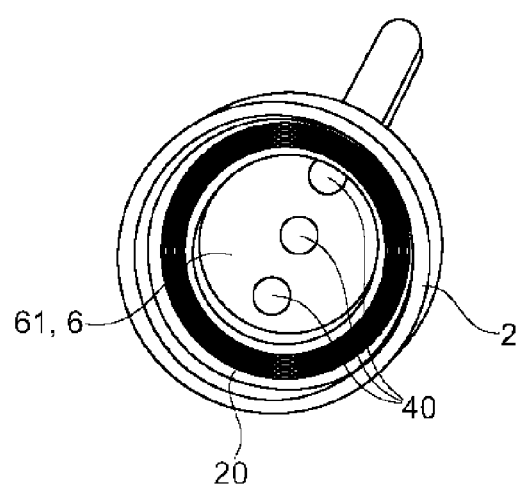
Fig. 3        Fig. 4

APPLICATOR AND A DYE KIT COMPRISING SAID APPLICATOR

CROSS-REFERENCE TO RELATED APPLICATIONS

This application is a National Stage Entry of International Application No. PCT/SE2015/050135, filed on Feb. 6, 2015, and claims the benefit of and priority to SE 1450128-2, filed Feb. 7, 2014 which are hereby incorporated by reference into this application in their entirety.

FIELD OF THE INVENTION

The present invention relates to an applicator for applying a product to head hair, said applicator comprising a neck portion and a flexible/elastic spatula, said neck portion comprising inner threads and an upper end and said spatula comprising a free end at a distal end from said neck portion, said free end comprising an edge extending in a substantially orthogonal direction to the extension of the spatula, said edge having at least one dispensing opening, the invention also relates to a kit for applying a product to head hair, comprising a container.

BACKGROUND INFORMATION

Many people today will bleach or dye their hair, sometimes at a salon, but since the bleaching/dyeing is needed to be done regularly to cover the outgrowth, for example every four weeks, it will be quite expensive and bleaching/dyeing at home is a common complement between visits at a salon. In connection with the bleaching/dyeing it occurs a lot of disadvantages. It is normal to get color/bleach stains on the skin, clothing and bathroom fittings. It also takes time to apply to the hair and it is difficult to apply with precision. For best results, it also requires a lot of tools: a graduated glass, a bowl to mix the color or bleach components in, brush, gloves, comb, greasy cream to protect the skin and paper to wipe off the paint spills. All these tools leave a lot to clean afterwards. In other words, to dye/bleach the hair, for many, is a messy procedure, and many are reluctant to do this. There are some tools to use in hair dyeing/hair bleaching. For example US 2001/0042553 A1 discloses an application member for applying a product to a surface of a body. The application system comprises a reservoir containing the product and an application member which application member is removably attached to the reservoir. The application member comprises a base portion and a plurality of teeth, each of the teeth have a free end provided with a dispensing orifice. The orifice communicates by means of a passage inside the teeth with the reservoir for applying the product contained in the reservoir.

US 2004/0016440 A1 discloses an applicator assembly for applying a product such as a cosmetic product. The assembly comprises an applicator nozzle with an attachment portion configured to attach the nozzle to a receptacle that contains the product. The nozzle comprises an arrangement of teeth and at least one of the teeth defines a channel configured to be placed in flow communication with product contained in the receptacle. The teeth comprise a lateral outlet aperture on the exterior.

WO 01/35789 A1 discloses a container top for applying liquid hair treatment agent to the hair. The container top comprises several hollow teeth on a tooth base. The teeth have an inner channel which is provided with at least one exit opening and between the hollow teeth there are arranged comb teeth.

FR 1185116 discloses an applicator for especially hair dyes. The applicator is screwed onto a container and has a hollow interior. When pressing the container the product is ejected through openings in the applicator.

Although there are some tools available on the market, they are all associated with disadvantages such as: non precise application, one still have to use tools such as ones fingers or a brush to distribute the dye and the risk of spilling dye. Therefore there is a need for an improved applicator when dyeing/bleaching the hair.

SUMMARY OF THE INVENTION

It is an object of the present invention to overcome or at least minimize at least one of the drawbacks and disadvantages described above and this can be obtained by an applicator in accordance with claim 1.

Thanks to this invention the process of bleaching/dying the hair becomes much easier and provides a number of advantages as one need not use any additional tools besides the inventive applicator and wastage of dye and dye packages are reduced.

According to one aspect of the invention the spatula comprises a free end with dispensing openings so dye may flow out from the dispensing openings and the spatula may be used to distribute the dye making it easier and faster to dye the roots/outgrowth.

According to another aspect of the invention the edge of the spatula may be somewhat concave which has the advantage that the dye comes closer to the scalp immediately and makes the dying faster with a better result.

According to still another aspect of the invention the spatula comprises internal channels extending from the edge to an inner bottom of the neck portion which gives a flow communication between the container and the dispensing openings, the advantage with the internal channels is that in principle no dye remains in the spatula after dying which is the case if the spatula would have been hollow, less waste of dye.

According to yet another aspect of the invention the internal channels are tapered conical which provides the advantage that when the pressure, exerted on the container, is released, the dye in the internal channels is sucked back into the container and prevents dye from running outside the applicator.

According to another aspect of the invention the internal channels are designed to match the viscosity of the dye in a way that the dye does not flow out from the dispensing openings if not a pressure is exerted on the container.

According to still another aspect of the invention the neck portion comprises inner threads which make it possible to arrange it on a container again and again in a simple manner.

According to another aspect of the invention the spatula has a thickness, width and flexibility/elasticity making it suitable to distribute the dye on the roots/outgrowth.

According to another aspect of the invention the kit comprises a container and an applicator making it possible to use subsets of dye or bleach and just use the amount dye/bleach needed for the moment which is economically and environment-friendly.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a side view of an applicator according to the invention,

FIG. 2 is a front view of an applicator according to the invention,

FIG. 3 is a perspective view of an applicator according to the invention,

FIG. 4 is a perspective view seen from underside of the applicator according to the invention.

DETAILED DESCRIPTION

Figure 5:
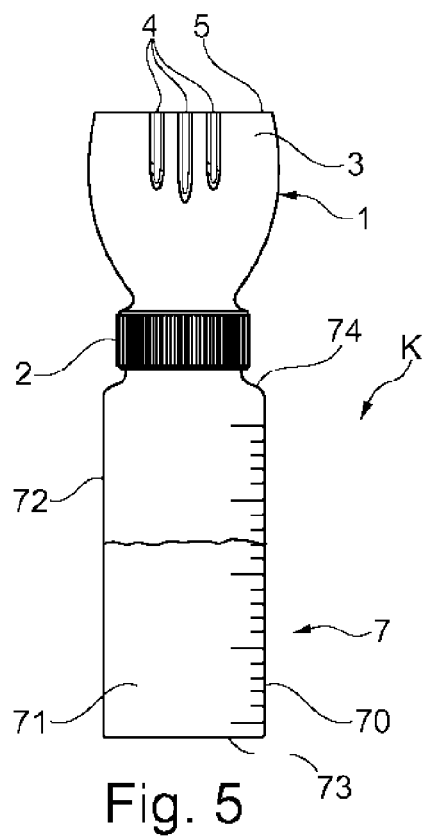
FIG. 5 is a side view of an applicator kit according to the invention.

The following detailed description, and the examples contained therein, are provided for the purpose of describing and illustrating certain embodiments of the invention only and are not intended to limit the scope of the invention in any way.

In FIG. 1 is seen, in a side view, an applicator 1 according to the invention in a first embodiment. The applicator 1 is preferably one integrated unit and comprises a neck portion 2 and a spatula 3. The inside of the neck portion 2 is cylindrical and has an inner diameter D in the interval 10-40 mm, more preferred in the interval 15-35 mm and most preferred in the interval 20-30 mm. The outside 23 of the neck portion 2 may be arranged with a roughed surface, e.g. grooves, to provide a secure grip. The inside of the neck portion 2 is arranged with threads 20, see FIGS. 4 and 6, to allow the applicator 1 to be threaded on e.g. a container 7. The upper end of the neck portion 2 comprises a substantially flat upper side 21 from which the spatula 3 extends in a substantially orthogonal direction, in the form of a mainly flat shaped body portion 31. The spatula 3 has in its free end 30, the distal end of the spatula 3 from the neck portion 2, a thickness T in the interval 0.5-10 mm, more preferred in the interval 1-6 mm and most preferred in the interval 1.5-3 mm.

FIG. 2 shows the applicator 1 in a front view and the applicator 1 has a height H in the interval 30-90 mm, more preferred in the interval 40-80 mm and most preferred in the interval 50-60 mm. The flat shaped body portion 31 of the spatula 3 in the described embodiment has a width W in its free end 30 that is somewhat broader than the diameter D of the neck 2. The width W is in the interval 10-60 mm, more preferred in the interval 20-50 mm and most preferred in the interval 25-45 mm. The skilled person realises that the width W of the spatula may be broader, narrower or as wide as the neck portion 2. Between the neck portion 2 and the flat shaped body 31, at the lower end of the flat shaped body portion 31, the applicator 1 comprises a bridging portion 8. The flat shaped body portion 31 is less wide than the diameter D in the bridging portion 8 and presents side edges 32, 33 that diverge whereby forming a waist-like portion 9. The free end 30 of the spatula 3 comprises an edge 5. In one possible embodiment the edge 5 is somewhat concave in a longitudinal direction to better follow the shape of the head, come closer to the scalp when applying and for a better result in dyeing/bleaching the roots/outgrowth. At the edge 5 there is arranged between 1-7 dispensing openings 4, in this described embodiment there are three dispensing openings 4. The dispensing openings 4 are arranged along the edge 5, preferably symmetrically arranged in the middle portion of the edge 5 giving the advantage that the outer portions of the edge 5 that are not arranged with dispensing openings 4 are used to distribute the dye when moving the spatula to a portion of the outgrowth adjacent the recently dyed portion. In that way is avoided that too much dye is applied at the same portion of outgrowth. It is of course possible to arrange the dispensing openings 4 in other ways, for example to evenly arrange the dispensing openings 4 along the total length of the edge 5. The dispensing openings 4 communicate through internal channels 50 that extend through the flat shaped body 31 (see FIG. 6) with inlet openings 40 in the interior of the neck portion 2, on the lower side 61 of a bottom 6 (see FIG. 4) of the bridging portion 8. The bottom 6 may be flat, but preferably the bottom 6 is cup shaped, thereby promoting the flow towards the inlet openings 40. There is arranged one internal channel 50 per each dispensing opening 4 in this embodiment.

In an alternative embodiment, the bridging portion also comprises supporting members 34, 35 on opposite flat sides of the flat shaped body 31. The supporting members 34, 35 resemble conical halves that extend on each flat side of the flat shaped body 31, thereby providing stability and flexural strength to the spatula 3. Due to the supporting members 34, 35 arranged in the bridging portion 8, the applicator 1 has sufficient strength even though the internal channels 50 run through this portion. Otherwise there is a risk that there would be too little material in this portion and other technical solutions would be required, e.g. a thicker spatula, less flexural material or constructing the applicator in different materials, which would significantly complicate the manufacturing process and make the applicator more expensive.

The upper side 21 of the bottom 6 presents an annular body portion 25 at the orifice of the bottom 6 that connects the bottom 6 with the upper end of the threaded portion 20 of the neck portion 2. A sealing edge 24 encircles the interior of the bottom 6 at the end of the threaded portion 20. Further, radially inside the sealing edge 24, there is shown a cylindrical sealing lip 22 intended to seal against the inside of a bottle neck. The product e.g. dye/bleach that will be applied is running through the internal channels 50 which gives the advantage that it will be less wastage of dye than if the spatula 3 would have been hollow because dye in that case would have been remained in the hollow spatula and rinsed away at cleaning, it is also easier to control the outflow of the product thanks to the internal channels 50.

The applicator 1 is preferably molded in one integrated piece which gives the advantage that it becomes more economical to produce because several parts are not needed to be assembled. It will also be easier to clean when there are no seams or loose parts to disassemble before cleaning. The applicator 1 is preferably made in an elastic material e.g. rubber, silicon, polyurethane or other types of flexible/elastic material. A flexible/elastic material will be more comfortable to the head when the applicator 1 is pressed against the scalp, if a hard material is used it may cause irritation to the skin that is aggravated by the application of hair dye or bleach. The flexible/elastic material also allows for a more precise application of the hair dye because the material bends and gets closer to the scalp. It's good to get as close to the scalp as possible to dye the outgrowth for a good and quick result. Getting as close as possible to the scalp at the first/initial application makes the whole application of the area faster. As the flexible/elastic material bends when pushed towards the scalp you can push harder and therefore allow the dye/bleach to penetrate several layers of hair which makes the procedure faster. No gasket is required between the bottle and the applicator 1 to minimize leakage because the material normally is elastic. Depending on the flexibility/elasticity of the material in the applicator 1 it is also possible, if a stiffer material is used, that a gasket may be used.

Figure 6:
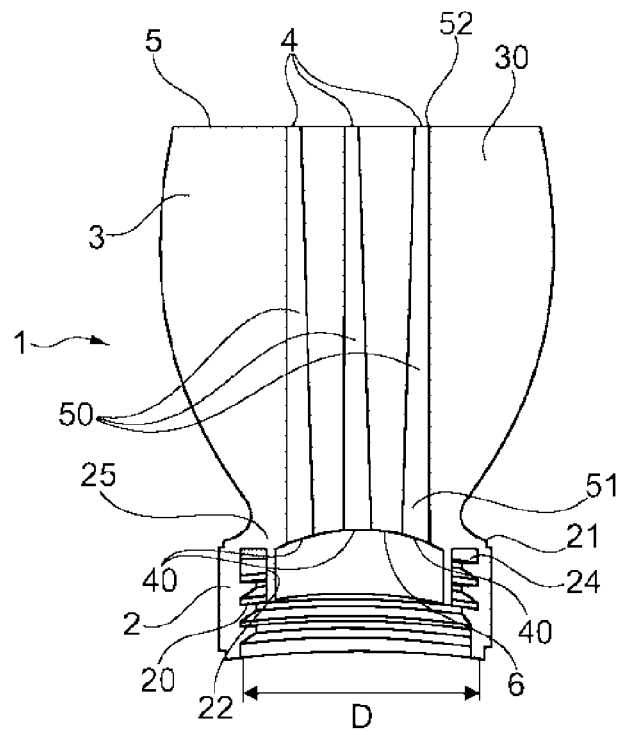
FIG. 6 is a cross sectional view of an applicator according to the invention.

In FIG. 3 is seen how the dispensing openings 4 are arranged at the edge 5 of the spatula's free end 30, which provides a more precise application of the dye and better control of the product being applied. The applicator 1 comprises at least one internal channel 50, preferably at least three internal channels 50 to feed a sufficient dye volume to the applicator edge 5 for a faster application. In FIG. 6 is seen a cross sectional view of the applicator 1. It is seen how the internal channels 50 extends from the bottom 6 of the neck portion 2 through the spatula 3 to the edge 5 of the free end 30 of the spatula 3. The internal channels 50 are preferably tapered conical with the widest end 51 of the internal channels 50 at the neck portion 2 end and the narrowest end 52 of the internal channels 50 arranged at the edge 5. The diameter of the widest end 51 of the internal channels 50 are in the interval 2-5 mm in the described example the diameter of the widest end 51 is 3 mm. The diameter of the narrowest end 52 of the internal channels 50, i.e. at the distal end/openings 4, are in the interval 1.5-4 mm, in the described example the diameter is 2 mm. Thanks to the design of the internal channels 50 a suction, created upon release of a squeeze force causes the dye to retract from the edge 5 of the spatula 3. Advantageously, this minimizes the risk of run-off of the dye on e.g. sink or skin. It also minimizes the proportion of dye wastage because the dye is being retracted back into the bottle and do not remain in/on the applicator 1 because of the suction effect. The conical tapered internal channels 50 also slow up the dye so that the outflow of dye is controlled by the amount of pressure that occurs in the bottle when squeezing it.

Figure 7:
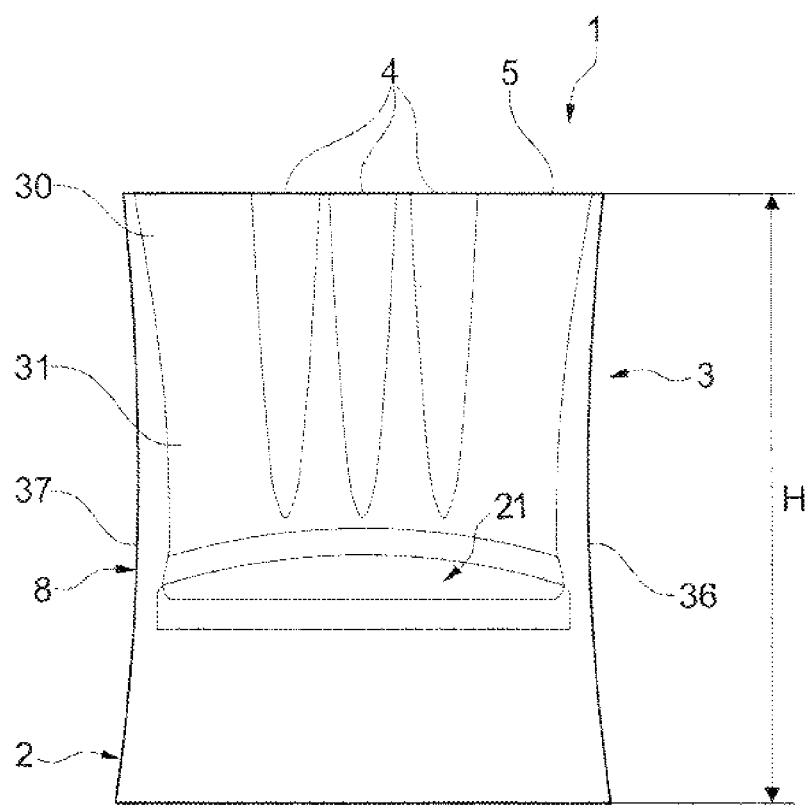
FIG. 7 is a front view of an applicator according to the invention.

In FIG. 7 is seen, in a front view, an applicator 1 according to the invention in a preferred embodiment. The difference compared to the above described applicator is that the flat shaped body 31, in the bridging portion 8, is as wide as the neck portion 2. The side edges 36, 37 of the flat shaped body 31 are somewhat curved outwardly which provides a sharper corner where the edge 5 and the side edges 36, 37 meet. The sharper corner gives a better possibility of a more precise application at particularly challenging parts, such as the hairline in front of the ears (the sideburns). The skilled person realizes that the side edges 36, 37 may also be straight or somewhat curved inwardly. In the latter case, the flat shaped body 31 is narrower at the edge 5 than at the bridging portion 8. The flat shaped body 31 in FIG. 7 extends across the upper side 21 of the neck portion 2, thereby obtaining a strong and stable attachment in the bridging portion 8. The attachment of the spatula 3 does not require any supporting members. No supporting members provide advantages in the manufacturing process e.g. avoiding blistering and deformations which may occur because of too thick material, and the spatula 3 flexes easier and acts more like a brush which facilitates the application.

The elasticity/flexibility of the material used in the applicator 1 may be equivalent to 25-85 in the Shore A scale. It may also be possible to have different elasticity/flexibility of the material in the neck portion 2 (screw cap part) and the spatula 3. This gives the advantages that the spatula 3 has a elasticity/flexibility which makes it easy and smoothly to use the spatula to apply the dye (or bleach) on the roots/outgrowth and the neck portion 2 may have a different elasticity/flexibility, a relative minor softness compared to the spatula 3, which makes the seal against the bottle better and less leakage of dye when squeezing on the bottle.

In FIG. 5 is seen an applicator kit K according to the invention, for applying a product 71 e.g. dye or bleach, to the hair on an individual's head. The kit K comprises an applicator 1 as described above and a container 7, such as a plastic bottle, preferably configured to be hold easily in one hand of the user. It is also preferred that the container 7 has a substantially flat bottom in its lower end in order to be able to set down the kit on a base. The container 7 is preferably flexible configured to be squeezed to cause the product 71 to pass through the internal channels 50 in the applicator 1 and flow out via the dispensing openings 4. The container 7 comprises a body 72 preferably provided with ml/fl oz-dash 70 and the body 72 may have an oval or circular cross-section and a closed base 73 in its lower end. In the upper end the container 7 may form a shoulder 74 extending in the form of a cylindrical neck arranged with outer threads. The applicator 1 is removably attached to the container 7 via the internal threads 20 on the applicator 1 and outer threads (not shown) on the bottle neck. The internal channels 50 are preferably designed/dimensioned in such a way that the product, contained in the container 7, does not flow out through the dispensing openings 4 unless a squeezing force is exerted to the container 7, for example by the users hand. The dimension is adapted to/dependent of the viscosity of the dye. In this way, the spatula 3 may be used to distribute the dye on the hair without excess dye flows out from the dispensing openings 4.

A big advantage when you want to dye outgrowth is that when using the inventive kit it is possible to use subsets of dye components (or bleach) from packaging that would normally be consumed all at one time. Parts of the dye liquids are poured directly into the container 7 that preferably is provided with ml dash for easier dosing. After that, the container 7 is sealed, for example with a screw cap, and is shaken to mix the dye components, then the screw cap is replaced with the inventive applicator 1 and the roots/outgrowth may be dyed. It is also possible to cover the dispensing openings 4 with a finger or the like for, when shaking, to facilitate the dye/bleach process yet more. When the applicator 1 is arranged at the container 7 the inner bottom 6 of the neck portion 2 is in the vicinity of the opening of the container 7 which also leads to less waste of dye/bleach. When applying the dye/bleach 71, contained in the container 7, to the outgrowth the user may hold the kit K in one hand and direct the applicator 1 downwards against the scalp such that the edge 5 with the dispensing openings 4 are abutting the scalp. By exerting a suitable squeeze force, on the container 7, the user force the dye 71 through the internal channels 50 and out through the dispensing openings 4. When enough dye has left the dispensing openings 4, the squeeze force is released and the spatula 3 is used to distribute the dye evenly on the roots/outgrowth. The spatula 3 has an elasticity/flexibility that allows the spatula 3 to distribute the dye and at the same time adapt to the scalp without being too soft. The spatula 3 is thus used as a paintbrush to distribute the dye from the scalp and outwards on the outgrowth. There is thus no need to use a further tool such as a separate brush or the fingers to distribute the color since the user uses the spatula 3 for this purpose. When the dyeing/bleaching is completed there are only two main things to clean, the applicator 1 and the container 7. Preferably the applicator 1 and the container 7 is rinsed by water and after that the container 7 is filled with water that is squeezed out from the container 7 through the internal channels 50 and in that way cleans the interior of the applicator 1. In this way the whole applicator kit K is reused at every dye occasion.

Thanks to the invention the use of dye liquids is reduced because one package of dyeing/bleaching liquids is sufficient for several rounds of dyeing the roots/outgrowth which is economically and also good for the environment as it contributes to less chemical waste and waste from packaging. Today there are many people that dye all the hair at each dying occasion because it is so complicated, sticky and messy to just dye the roots/outgrowth. Thanks to the invention it is much easier and less sticky to dye the outgrowth which will lead to a better hair quality since all hair is not dyed at every occasion. Another advantage is that since the inventive applicator 1 speeds up the dye application the dye result becomes better since the dyed part of the hair being exposed to the dye almost equally long. Only dyeing/bleaching strategic parts (such as the temples or parting of the hair) of the outgrowth/roots will also minimize the amount of skin/scalp coming in contact with the chemicals which is desirable for many for different reasons.

As will be understood by those skilled in the present field of art, numerous changes and modifications may be made to the above described and other embodiments of the present invention, without departing from its scope as defined in the appending claims. For example, in the described preferred embodiment, there are three dispensing openings, the skilled person realizes that it could be more or less then just three dispensing openings. The skilled person also realizes that the product to be applied may be a dye (adding pigment in the hair) or a bleach (removes the hair's existing pigment). It may also be other products that shall be applied, for example it may be medicinal agents, creams/oils for example against dry scalp. It is also understood that the container may be a flexible configured tube, or similar, with maybe a welded bottom. Although it is advisable that the container has a flat bottom so it does not exclude that the applicator may be used on a tube or similar. The spatula may also have other designs than the one described in the figures, the transition between the neck and the spatula may be thinner and the spatula may be as width as the neck in the bottom and taper along the height so that the spatula is narrower in its free end than at the neck. The spatula may also extend in an angled direction from the neck which can provides better ergonomics. The applicator may also be made of other materials, such as plastic.

The invention claimed is:

1. An applicator for applying a product to head hair, said applicator comprising:
 a neck portion and a flexible/elastic spatula,
 said neck portion comprising inner threads and an upper end and said spatula comprising a free end at a distal end from said neck portion,
 said free end comprising an edge extending in a substantially orthogonal direction to the extension of the spatula,
 said edge having at least one dispensing opening, wherein said spatula mainly forms a substantially flat shaped body portion,
 between said neck portion and said substantially flat shaped body portion the applicator comprises a bridging portion,
 said bridging portion comprising a bottom extending in a substantially transversal direction to the neck portion,
 said substantially flat shaped body portion extending in a substantially orthogonal direction from said bottom,
 wherein said substantially flat shaped body portion comprises at least one internal channel extending from said at least one dispensing opening to at least one inlet opening arranged at the lower side of the bottom in the interior of the neck portion, wherein the bridging portion comprises a sealing edge adjacent the end of the threaded portion, said sealing edge encircling the interior of the bottom, radially inside the sealing edge, there is arranged a cylindrical sealing lip extending in an axial direction of the neck portion.

2. The applicator according to claim 1, wherein the at least one internal channel is conical with a widest end at said inlet opening and the narrowest end of the internal channel arranged at said dispensing opening.

3. The applicator according to claim 1, wherein the at least one internal channel is designed to match the viscosity on the dye in a way that the dye does not flow out from the dispensing opening if a pressure is not exerted on the container.

4. The applicator according to claim 1, wherein the neck portion and the spatula form one integrated unit.

5. The applicator according to claim 1, wherein the spatula has a thickness (T) in the interval 0.5-10 mm, a width (W) in the interval 10-60 mm.

6. The applicator according to claim 1, wherein said at least one dispensing opening is arranged along the edge, preferably symmetrically arranged, in the middle portion of the edge, and outer portions of the edge having an edge without dispensing openings.

7. The applicator according to claim 1, wherein there is arranged one internal channel per each dispensing opening.

8. The kit (K) according to claim 1, wherein an inner bottom of said bridging portion is arranged in the vicinity of an opening of said container containing said product.

9. A kit (K) for applying a product to head hair, comprising a container, wherein said kit (K) also comprises an applicator comprising:
 a neck portion and a flexible/elastic spatula,
 said neck portion comprising inner threads and an upper end and said spatula comprising a free end at a distal end from said neck portion,
 said free end comprising an edge extending in a substantially orthogonal direction to the extension of the spatula,
 said edge having at least one dispensing opening, wherein said spatula mainly forming a substantially flat shaped body portion,
 between said neck portion and said substantially flat shaped body portion the applicator comprises a bridging portion,
 said bridging portion comprising a bottom extending in a substantially transversal direction to the neck portion,
 said substantially flat shaped body portion extending in a substantially orthogonal direction from said bottom,
 wherein said substantially flat shaped body portion comprises at least one internal channel extending from said at least one dispensing opening to at least one inlet opening arranged at the lower side of the bottom in the interior of the neck portion, wherein the bridging portion comprises a sealing edge adjacent the end of the threaded portion, said sealing edge encircling the interior of the bottom, radially inside the sealing edge, there is arranged a cylindrical sealing lip extending in an axial direction of the neck portion.

10. The kit (K) according to claim 9, wherein said container is flexible and comprises a substantially flat bottom.

11. The kit (K) according to claim 9, wherein said container is flexible and comprises a tube or similar with a welded bottom.

\* \* \* \* \*